United States Patent [19]

Atkinson et al.

[11] Patent Number: 5,460,948
[45] Date of Patent: Oct. 24, 1995

[54] ASSAY OF SALICYLATES OR REDUCED PYRIDINE NUCLEOTIDES

[75] Inventors: Anthony Atkinson, Salisbury; Stewart R. Cambell, Cambridge; Peter M. Hammond, Alderbury; Helen C. Morris, Cambridge; John R. Ramsey, Salisbury; Christopher P. Price, Stapleford, all of England

[73] Assignee: The Public Health Laboratory Service Board, London, England

[21] Appl. No.: 108,805

[22] Filed: Aug. 19, 1993

Related U.S. Application Data

[63] Continuation of Ser. No. 943,984, Sep. 11, 1992, abandoned, which is a continuation of Ser. No. 543,745, filed as PCT/GB88/01063, Dec. 2, 1988, abandoned.

[30] Foreign Application Priority Data

Dec. 3, 1987 [GB] United Kingdom .................. 8728296

[51] Int. Cl.[6] .............................. C12Q 1/26; C12Q 1/00; C12Q 1/56; C12Q 1/54
[52] U.S. Cl. .................... 435/25; 435/4; 435/13; 435/14; 435/19; 435/22; 435/23; 435/26; 435/805; 435/810
[58] Field of Search .................................. 435/4, 13, 14, 435/19, 22, 23, 25, 26, 805, 810

[56] References Cited

U.S. PATENT DOCUMENTS 4,416,983  11/1983  Roder et al. ............................ 435/25

FOREIGN PATENT DOCUMENTS 0138530  4/1985  European Pat. Off. .

OTHER PUBLICATIONS

Analyst, Sastry et al, vol. 110, Apr. 1985, p. 395.
Longenecker et al Clin. Chem., vol. 30, No. 8, 1984, pp. 1369–1371.
Clinica Chimica Acta, Chubb et al, vol. 155, No. 3, Mar. 28, 1986, pp. 209–220.
Clinica Chimica Acta, vol. 155, No. 3, 1986, S. A. P. Chubb, et al, "An Enzyme Mediated, Colorimetric Method For The Measurement Of Salicylate" pp. 209–220.
Analyst, vol. 110, No. 4, 1985, C. S. Sastry et al, "Spectrophotometric Methods For The Determination Of O–Dihydroxybenzene Derivatives", pp. 395–398.
Clin. Chem., vol. 30, Nov. 8, 1984, Longenecker et al, "A Tableted Enzymic Reagent For Salicylate, For Use In A Discrete Multiwavelength Analytical System (Paramax™)", pp. 1369–1371.

Primary Examiner—Mindy B. Fleisher
Attorney, Agent, or Firm—Nixon & Vanderhye

[57] ABSTRACT

A method for the estimation of a salicylate in a sample is characterized by enzymatically converting the salicylate to a catechol by the action of a salicylate mono-oxygenase enzyme on the salicylate in the presence of a reduced pyridine nucleotide, reacting the catechol with a compound selected from compounds of formula I or amine or phenolic compounds of formulae II, III or IV

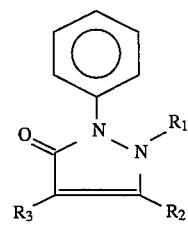

Formula I

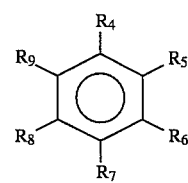

Formula II

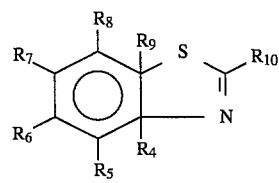

Formula III

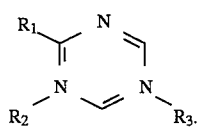

Formula IV

17 Claims, 6 Drawing Sheets

RATE OF COLOUR DEVELOPMENT FOR SALICYLATE ASSAY USING A COMBINED ENZYME AND COLOUR REAGENT.

CALIBRATION CURVE WITH SERUM CALIBRATORS FOR THE SALICYLATE ASSAY USING A COMBINED ENZYME AND COLOUR REAGENT.

VARIATION IN THE SALICYLATE ASSAY CALIBRATION CURVE.

STORAGE STABILITY OF THE ENZYME REAGENT
FOR THE TWO-REAGENT SYSTEM.

COMPARISON OF SALICYLATE RESULTS USING PROPOSED ENZYMATIC PROCEDURE AND ROUTINE COLORIMETRIC PROCEDURE.

ASSAY OF SALICYLATES OR REDUCED PYRIDINE NUCLEOTIDES

This is a continuation of application Ser. No. 07/943,984, filed Sep. 11, 1992, now abandoned which is a continuation of 07/543,745, filed as PCT/GB88/01063, Dec. 2, 1988, now abandoned.

This invention relates to a method for the estimation of salicylates or reduced pyridine nucleotides, and to a diagnostic kit adapted to facilitate the routine performance of said method.

There is a requirement to estimate the level of salicylate compounds, particularly the drugs ortho-acetyl salicylic acid (aspirin) and salicylic acid (which is commonly used as its sodium salt) in a biological fluid. In such cases, and especially where a patient is suffering from a drug overdose, it is important that the drug level in the body may be assessed rapidly so that an antidote or other treatment may, if necessary, be administered.

A number of methods for estimating salicylate in a sample or in a solution are known. For example, the salicylate ion can be reacted with the Folin-Ciocalteau reagent in a strongly alkaline solution to produce a blue colour which is then analysed colorimetrically (Smith & Talbot 1950, *Brit J Exp Path.* 31 65). This method, however, gives high and variable blank values in samples where salicylates are absent.

Alternatively, the salicylate ion can be reacted with ferric salts in acidic solution and the purple colour produced analysed by a colorimetric means. (Trinder 1954, *Biochem J.* 57, 301). This method too has disadvantages, and is subject to non-specific interference.

In another method of salicylate estimation, the salicylate is first converted enzymically to form pyrocatechol. The latter compound is then reacted with hydrazone and molecular oxygen in the presence of a second enzyme, tyrosinase, to form an azine dye. (Roder et al 1980, EP 0 054 146). The enzyme tyrosinase is known to oxidise monophenols other than pyrocatechol, and hydrazone may couple oxidatively with any resulting quinones to form a coloured product. Furthermore, the presence of other monophenols and particularly of tyrosine in unknown quantities may result in competition for binding sites on the tyrosinase enzyme, reducing the efficiency of the system.

In yet another method of salicylate estimation as disclosed in European patent application number 84306810.7, the salicylate is first converted enzymically to catechol. The catechol is then reacted with aminophenol under alkaline conditions to form an indophenol which is capable of quantitative estimation by colorimetric techniques. The aminophenol is however, unstable in alkaline conditions and it is therefore necessary to store it before reaction with catechol under acidic conditions. Furthermore unless the reaction of aminophenol with catechol is rapid, the alkaline conditions under which the reaction of aminophenol with catechol takes place can result in degradation of the aminophenol or side reactions of the aminophenol, which can give rise to inaccurate results.

A further problem with this technique is that it is not practical to provide it in the form of an efficient all in one reagent kit as the aminophenol would need to be kept under acidic conditions prior to assay and the indophenol product requires neutral and preferably alkaline conditions for its formation.

Ideally the components of a salicylate estimation method will be soluble in water, have a high speed of colour development when reacted and give good colour yield and high stability of the final colour.

It is one object of the present invention to provide a method for the estimation of salicylate by which the above disadvantages are overcome or at least mitigated, but which still produces an estimation of salicylate level sufficiently quickly to allow the method to be used in the determination of drug levels in the biological fluids of suspected overdose patients.

According to the first aspect of the present invention, therefore, there is provided a method for the estimation of salicylate in a sample characterised by enzymically converting the salicylate to a catechol by the action of a salicylate mono-oxygenase enzyme on the salicylate in the presence of a reduced pyridine nucleotide (especially NADH or NADPH) reacting the catechol with a compound selected from Formula I, II, III, and IV:

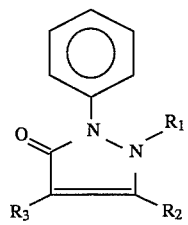

Formula I

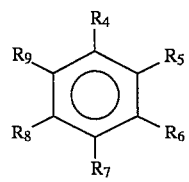

Formula II

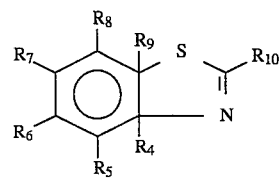

Formula III

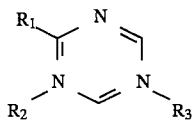

Formula IV wherein $R_1$ $R_2$ and $R_3$ are independently H, $-NH_2$ or $C_1-C_6$ alkyl, $R_4$ to $R_{10}$ are independently selected from H, alkyl, $-NH_2$, $-NR_{11}$ $R_{12}$, $-OH$, $-CH_2OH$, $-CHO$, $-COOH$, $-CO(CH_2)_nH$, $-CONH(CH_2)_n$ COOH or $-NH_2HOOCCOOH.H_2NC_6H_5$ where n is an interger from 1 to 5 inclusive and $R_{11}$, $R_{12}$ are independently selected from $C_1-C_5$ alkyl provided that where in formula II one of the groups $R_4$ to $R_9$ is $NH_2$ or $NR_{11}$ $R_{12}$ then at least one of the other groups $R_4$ to $R_9$ is selected from $C_1-C_6$alkyl, $-NH_2$, $-NR_{11}$ $R_{12}$ $-CHO$, $-COOH$, $-CO(CH_2)_nH$, $-CONH(CH_2)_n$ COOH or $-NH_2HOOCCOOHNH_2C_6H_5$, wherein Formula II does not include compounds falling into the scope of the term 'aminophenols', to form a dye the quantity of which can be estimated colorimetrically.

The quantity of the dye is then related to the quantity of the salicylate in the sample. Preferably the dye is estimated spectrophotometrically.

In Formula I preferably $R_1$ is methyl, $R_2$ is H and $R_3$ is $-NH_2$. In formula II preferably when $R_4$ is $-COOH$, $R_5$ is $-NH_2$ and $R_6$ to $R_9$ are H; when $R_4$ is $CONH(CH_2)_n$ COOH then n is preferably 1, $R_7$ is $NH_2$ and $R_4$, $R_5$, $R_8$ and $R_9$ are H; when $R_4$ is $-CO(CH_2)_nH$ then n is preferably 1, $R_7$ is $NH_2$ and $R_5$, $R_6$, $R_8$ and $R_9$ are H. In formula III $R_7$ is preferably $NH_2$ and $R_4$ to $R_6$ and $R_8$ to $R_{10}$ are preferably H. In formula IV $R_1$ and $R_2$ are preferably methyl and $R_3$ is —$NH_2$.

The word dye as used herein refers to a compound which absorbs electro-magnetic radiation over one or more of the ultra-violet (UV) visible or infra-red (IR) spectral regions.

The colour reaction will occur when using a range of amino or phenolic compounds selected from Formula I to IV at concentrations (0.5–50 mmol/L) but it is preferable to use 1.3–2.9 mmol/L.

The invention is based on the following reactions (using (NADPH) or NADH to exemplify the reduced pyridine nucleotide).

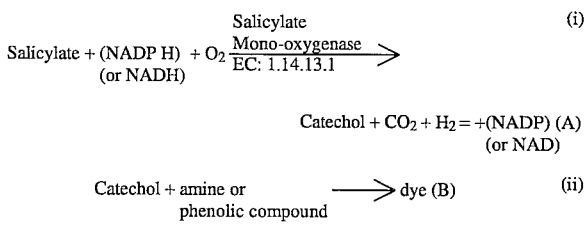

In reaction A above, the reduced pyridine nucleotide comprising either reduced nicotinamide adenine dinucleotide (NADH) or reduced nicotinamide adenine dinucleotide phosphate (NADP H) is converted to its respective oxidised form nicotinamide adenine dinucleotide (NAD) or nicotinamide adenine dinucleotide phosphate (NAD P).

This method of salicylate detection requires NADH or NADPH at a concentration in excess of the concentration of the highest salicylate standard for which the assay is linear. This requirement means that this method can also be used for the estimation of NADH or NADPH by including salicylate, in excess, in the enzyme reaction. This method can therefore, be used to detect the NADH or NADPH produced by the action of dehydrogenase enzymes on substrates such as glucose or lactates.

Conveniently the two reactions A and B, of the salicylate assay method can be performed simulataneously as a one step reaction where all the reagents are present together. Alternatively they may be performed successively as two steps, A, in which the formation of catechol takes place and B, in which the colour development of the catechol from reaction A with one of the specified amine or phenolic compounds takes place. The method is capable of being performed either manually or as part of an automated system.

The conversion of the salicylate to the catechol is catalysed by any salicylate mono-oxygenase enzyme defined as E.C.1.14.13.1 and named as salicylate mono-oxygenase (decarboxylating and hydroxylating) by the International Union of Biochemistry (Enzyme Nomenclature 1978, Academic Press, New York 1979). In the catalysed reaction the enzyme and the reduced pyridine nucleotide are present in excess.

The enzyme, salicylate monooxygenase, possesses NADH oxidase activity which effects the oxidation of NADH to $NAD^+$. Therefore, in order to be able to store the enzyme with NADH in an aqueous reagent it may be necessary to include a NADH regeneration system. For example:

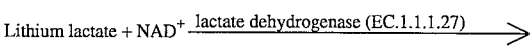

pyruvate + NADH

The storage stability of NADH can be further improved by the inclusion of chloride salts such as sodium chloride at a concentration of 10–5000 mmol/L and preferably about 100 mmol/L. Other suitable additives to restore $NAD^+$ to NADH to prevent the oxidation of NADH will be apparent to those skilled in the art.

If the assay reaction mixture contains high concentrations of metal ions then a metal chelating agent, preferably in the concentration 0.1 to 1.0 mmol should also be added to safeguard enzyme activity.

The enzyme reaction is however catalysed and accelerated by the presence of certain metal ions. The preferred metals for catalysing the enzyme reaction are manganese and cobalt.

Metal and ammonium ions may also be utilised to catalyse the colour reaction (B) of the catechol with the amine or phenolic compound to produce the dye. Metal ions which may be used for catalysing the development of colour include manganese, cobalt, copper, calcium and magnesium. Other suitable metal ions will be known to those skilled in the art. The concentrations of these colour development ions is usually in the range 0.01–50 mmol/L and preferably 0.1–0.25 mmol/L. Such concentrations of ions will however be variable with the individual assay in question.

Preferably the metal ions are provided in a compound which is readily soluble within an assay mixture and with the samples to be tested. The metal ions may, for example be derived from acetates such as cobalt acetate or alternatively other suitable compounds known to those skilled in the art provided that any counter ions to the metal ions do not interfere with the enzyme reaction or any other part of the assay technique.

Where the salicylate is present in the form of an acetylated derivative, it should first be converted to its non-acetylated form by hydrolysis of the acetylated derivative for example in a reaction catalysed by any enzyme of the type defined as EC: 3.1.1.2. and named as arylester hydrolase by the International Union of Biochemistry (reference as above). The conversion of catechol to dye (B) is performed by reacting the catechol with an amine or phenolic compound as specified above. Preferred amines in decreasing order of preference, are 4-aminophenazone (1), 2-aminobenzoic acid(II), 4-hippuric acid(II) 4-aminoacetophenone(II) and 6-aminobenzothiazole(III).

In a particularly preferred embodiment the reaction of catechol with 4-aminophenazone is fast, highly specific, and produces a relatively colour-stable dye. Preferably, the conversion of catechol to dye is performed in a substantially aqueous solution, at a neutral or, which is preferred, an alkaline pH. The colour reaction is more preferably performed within the pH range 8–14 and may use one or more buffers at concentrations of between 0.025–1.0 M/L and preferably 100 mmol/L.

In a preferred embodiment of the present invention the conversion is effected at a pH of 10. The types of buffer which may be used include, carbonate-bicarbonate, borate, glycine, diethanolamine, glycylglycine, sodium phosphate, potassium phosphate, Tris HCL, 2-N cyclohexylamino ethanesulphonic acid (CHES), 2-amino-2-methyl-1-propanol (AMP), 2-amino 2-methyl-1,3-propanediol (AMPD), N-Tris (hydroxymethyl) methyl-3-amino propanesulphonic acid (TAPS), 3 cyclohexyl(amino) -1-propanesulphonic acid (CAPS), N-2-hydroxyethyl-piperazine N-2-ethanesulphonic acid (HEPES) and N-2-hydroxyethyl-piperazine-N-3-propanesulphonic acid(EPPS).

The wide pH range of the salicylate monooxygenase enzyme (6.0–10.5) enables the enzyme reaction to take place under various pH conditions preferably alkaline and hence both the enzymic reaction(A) and the colour reaction (B) may take place in the same solution in a one step process, eg at the preferred pH of 10.

Alternatively, in a two step process the enzyme reaction may be carried out in a solution of appropriate pH which may also contain the amine or phenolic compound and the pH may then be adjusted for the colour reaction (B) eg by mixing the solution with sodium carbonate solution or a suitable alternative alkali such as sodium hydroxide at concentrations of 25–500 mmol/l preferably 120–250 mmol/L.

In an especially preferred embodiment of the invention the production of dye is effected in the presence of a buffer CHES and most preferably at buffer pH 10. This embodiment is particularly preferred for use with a single step salicylate estimation method which uses aminophenazone and especially 4-aminophenazone for colour development with the catechol.

In a further especially preferred embodiment of the invention the production of dye is effected by mixing sodium carbonate buffer with an enzyme reagent containing EPPS at a preferred pH of 8.6 and which has been used to convert the salicylate to catechol.

The reagents especially the enzyme, for a single step salicylate estimation assay are preferably provided in a lyophilised form. To prevent the reagents reacting with themselves before addition of a sample for salicylate assay.

In a preferred embodiment of the method of the invention, the reagents are deposited as successive frozen layers on a solid substrate which may conveniently be the wall of a container such as a storage vial, and the reagents are then lyophilised.

When the formation of the dye is carried out under conditions appropriate to allow a maximum rate of colour formation, it may be completed in about six minutes with serum samples.

Once produced, the dye is generally stable for at least one hour. However in certain cases, especially two step processes it may be preferable to add surfactants to improve the stability of the reaction product. Suitable surfactants include various salts of $C_{14}$–$C_{16}$ alpha olefin sulphonates such as Witconate AOS Li8, Witconate SES and Witconate 60L. Other suitable surfactants will be apparent to those skilled in the art. The surfactants if present are preferably in the range 0.005–5% and most preferably 0.05%.

The colour-producing reaction with an aryl amine of the type specified especially 4-aminophenazone, is highly specific. No interfering colour formation is observed in the reaction of the specified aryl amines with salicylate, acetylated salicylate, acylanilides, such as hydroxy-acetanilide, or with tyrosine. The present procedure, therefore provides a rapid and specific method for the determination of salicylate which will be particularly useful when the salicylate is present in biological fluids.

The spectrophotometric analysis of the dye may be carried out at any wavelength at which the dye absorbs, but is preferably carried out at the wavelength of maximum absorption. When a dye is formed by reaction of catechol with 4 aminophenazone this wavelength is 520 nm.

The present method of detecting salicylates will have many applications, but will be of particular use when a rapid but routine method of analysis is required, especially when the fluid in which the salicylate is present contains other constituents which are known to interfere in alternative methods of analysis. The present method will be particularly useful in the medical field for the detection of analgesic formulations based upon the drug salicylate. In this case the salicylate will tend to be in admixture with other drug derivatives that are known to interfere in the traditional means of rapid analysis.

The requirement for a co-factor, especially either NAD P H or NADH, in the enzymatic conversion of salicylate to catechol by salicylate monooxygenase, means that the present reaction scheme may also be employed in the estimation of a reduced pyridinenucleotide, especially either NADH or NAD P H. Examples of reactions where NADH or NAD P H may be produced (and then estimated) include the action of dehydrogenase enzymes on substrates such as glucose or triglycerides, or lactate.

Accordingly, the present invention further provides in a second aspect of the present invention a method for the estimation of a reduced pyridine nucleotide (especially NADH or NAD P H) in a sample comprising enzymically converting a salicylate to a catechol by the action of a salicylate mono-oxygenase enzyme on the salicylate in the presence of the reduced pyridine nucleotide, reacting the catechol with an amine or phenolic compound of the type specified to form a dye, and estimating the quantity of the dye colourimetrically, the quantity of the dye being a measure of the reduced pyridine nucleotide in the sample. Preferably the dye is estimated spectrophotometrically.

The method for estimating a reduced pyridinenucleotide is also based on reactions (A) and (B) above. However, in this case, unlike the estimation of salicylate (when enzyme and reduced pyridine nucleotide are in excess), the salicylate and the enzyme are present in excess. As before, the catechol is conveniently converted to a dye by reaction with an amine or phenolic compound of the type specified above, preferably one of the preferred amines referred to above, especially 4-aminophenazone.

When the reduced pyridine nucleotide is produced by the action of a dehydrogenase enzyme on a substrate, the estimation of the nucleotide produced may be used to estimate the amount of the substrate present. The use of the method of estimation of reduced pyridine nucleotide in this way is another aspect of the invention.

In order to further facilitate the use of the present methods of analysis in a routine manner, especially in medical techniques, the invention further provides a diagnostic kit for use in the estimation of a salicylate, or a reduced pyridine nucleotide (especially NADH or NAD P H) by a process of the present invention comprising:

a. a salicylate mono-oxygenase enzyme suitable for the conversion of salicylate to catechol in the presence of a reduced pyridinenucleotide, b. an amine or phenolic compound suitable for the conversion of the catechol to a dye as specified above, preferably one of the preferred amines mentioned above, especially 4-aminophenazone.

As outlined above, the salicylate mono-oxygenase enzyme is any of those defined as EC:1.14.1.13.1 by the International Union of Biochemistry. The amine or phenolic compound is preferably aminophenazone and especially 4-aminophenazone.

The enzyme and other reagents may be in solution, preferably aqueous solution. In this case, in order to retain the activity of the salicylate mono-oxygenase enzyme over prolonged periods of time, the enzyme solution preferably contains glycerol, or may be lyophilised preferably in the presence of a protective agent.

This protective agent may be a sugar, most especially glucose, lactose, raffinose or a polysaccharide.

Such a kit may comprise a single solution containing all the reageants necessary for steps (A) and (B), eg the enzyme, NADH or NADPH, buffer, catalyst and the aryl amine at a suitable pH. Alternatively the kit may comprise two separate solutions eg one containing all the reagents necessary for steps (A) and (B) and another containing an alkali to adjust the pH.

Alternatively, the enzyme and other reagents may be in an immobilised form, eg impregnated onto a solid or a semi-solid support. In this case a porous material, such as paper, is particularly preferred. Such a kit may be for use manually or with automated analysers. The advantage of the latter being the ability to operate with small sample volumes.

In order to further retain the activity of the enzyme, it may be stored at low temperature (5° to −20° C.) either with the other components of the kit or separately from them.

The amine or phenolic compound may also be present in the kit in the form of a solution preferably an aqueous solution. Alternatively the amine or phenolic compound may be immobilised eg impregnated onto a solid or semi-solid support. In this case a porous material, such as paper, is particularly preferred.

In one embodiment of the present kit both the enzyme and the amine or phenolic compound are impregnated onto a porous material, such as paper, which is then used in the form of a test strip.

Alternatively the kit may contain the reagents in a form suitable for dipstick assaying where the reagents may for example be immobilised perhaps as mentioned above or encapsulated or entrapped to provide a convenient means for storage and conducting assays for salicylate, reduced pyridine nucleotide or substrate consumed by the action of dehydrogenase enzyme.

In order to facilitate the use of the kit of this invention, each kit may be supplied with a set of instructions setting out the steps involved in the assay procedure.

The application of the present process is further illustrated by the following examples with reference to the following figures, of which:

Figure 1:
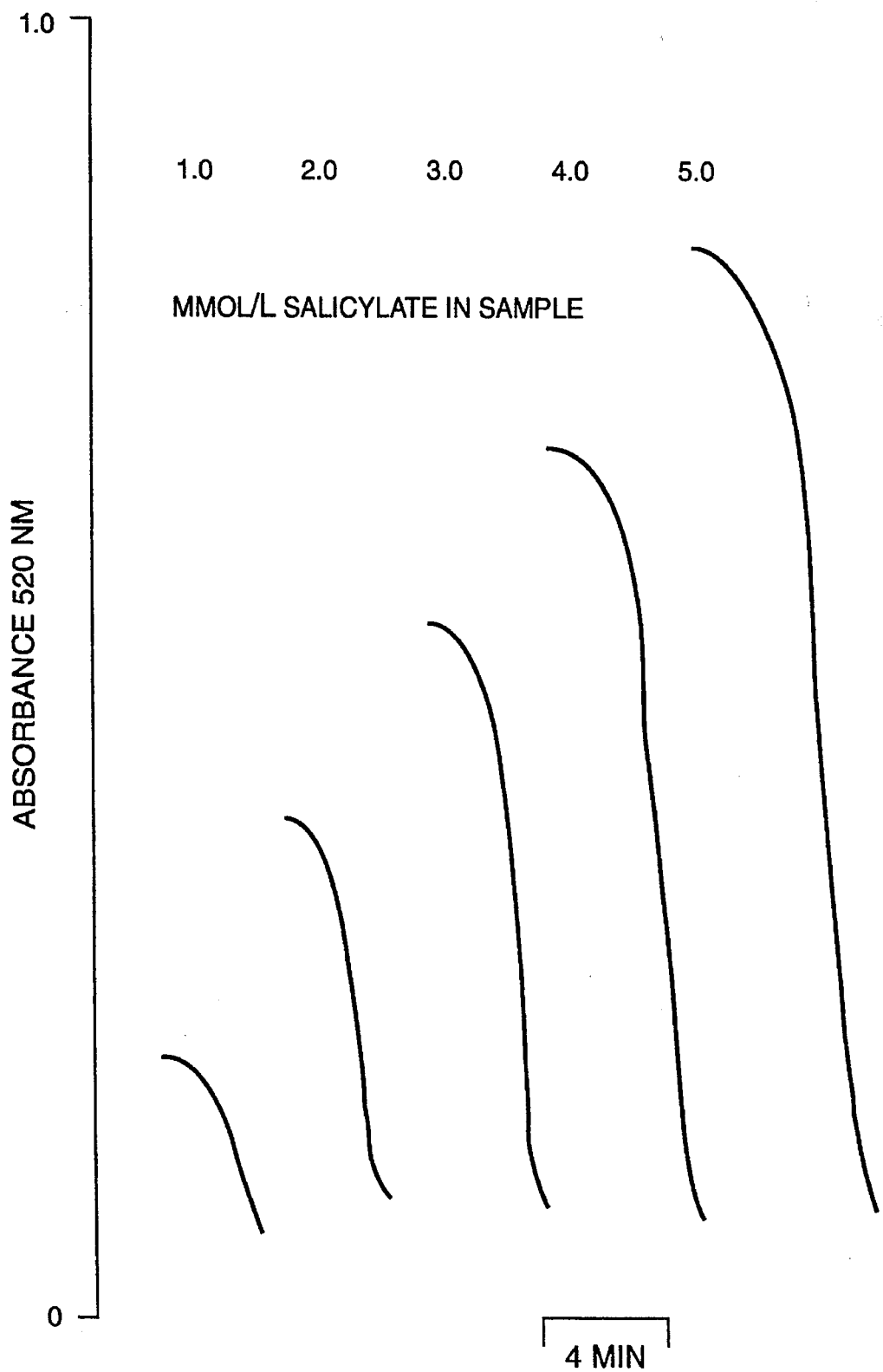
FIG. 1 shows the rate of colour development for salicylate assay using a combined enzyme and colour reagent.
Figure 2:
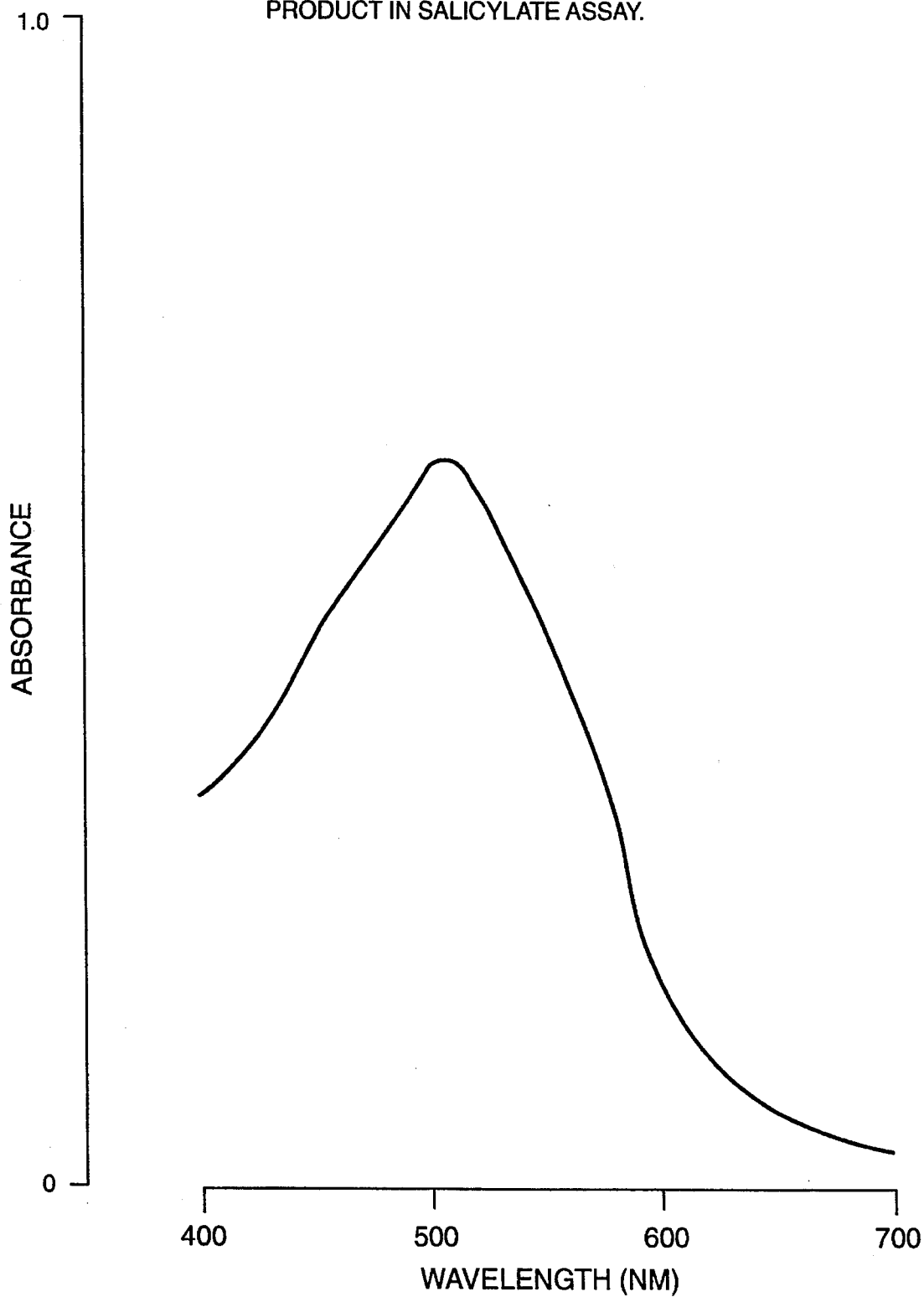
FIG. 2 shows a spectrum of the final reaction product in a salicylate assay.
Figure 3:
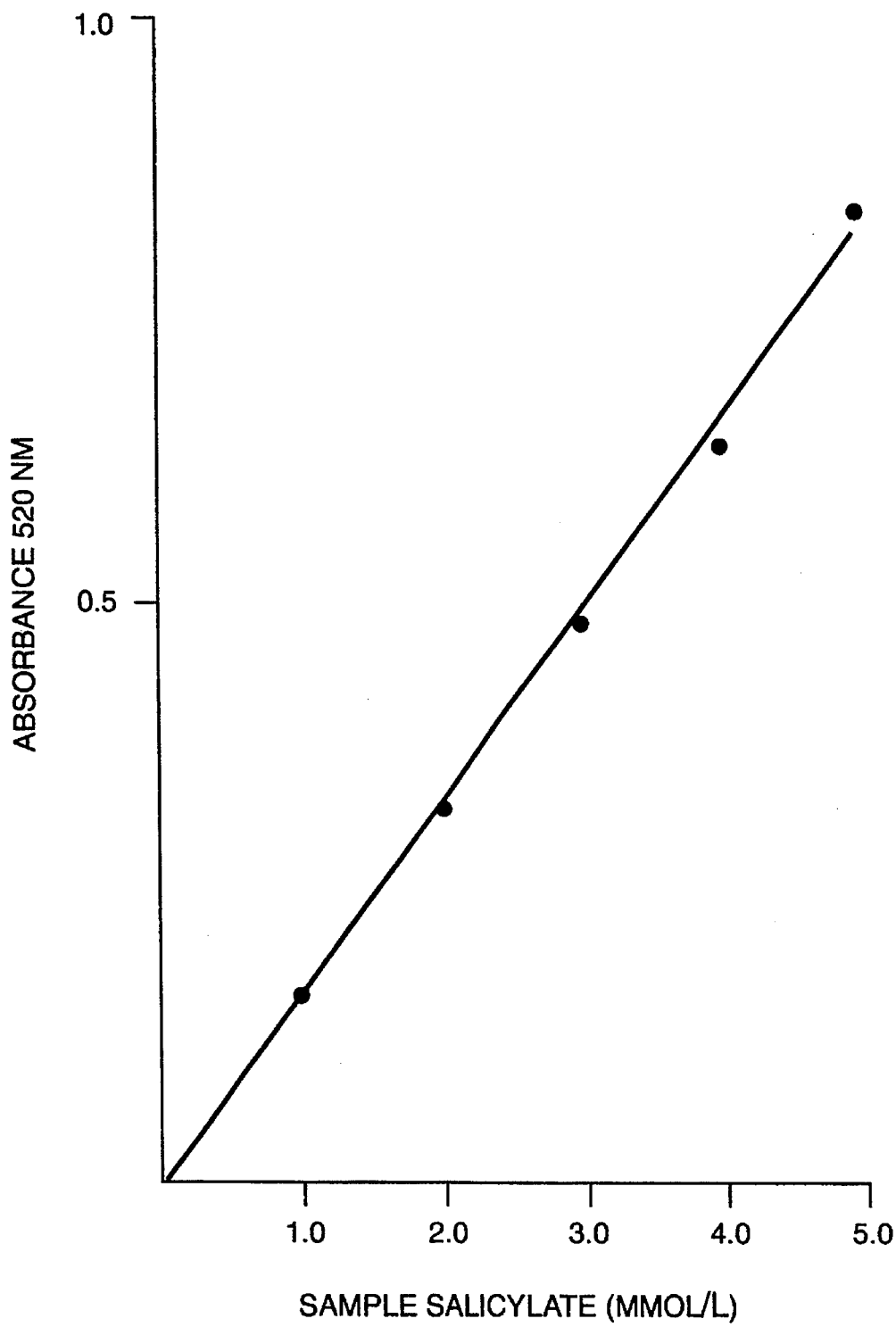
FIG. 3 shows a calibration curve with serum calibrators for the salicylate assay using a combined enzyme and colour reagent.
Figure 4:
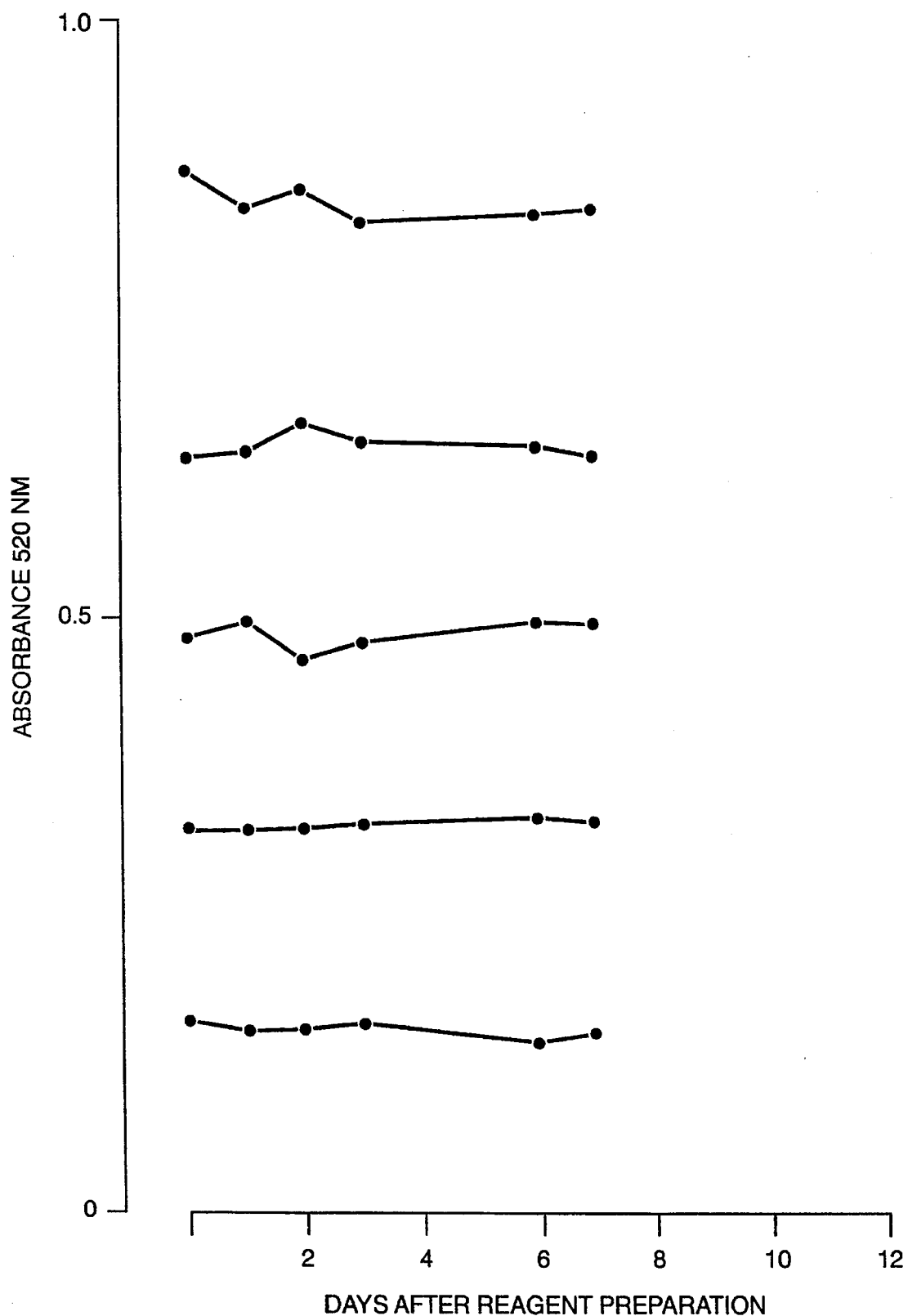
FIG. 4 shows the variation in the salicylate assay calibration curve with time.
Figure 5:
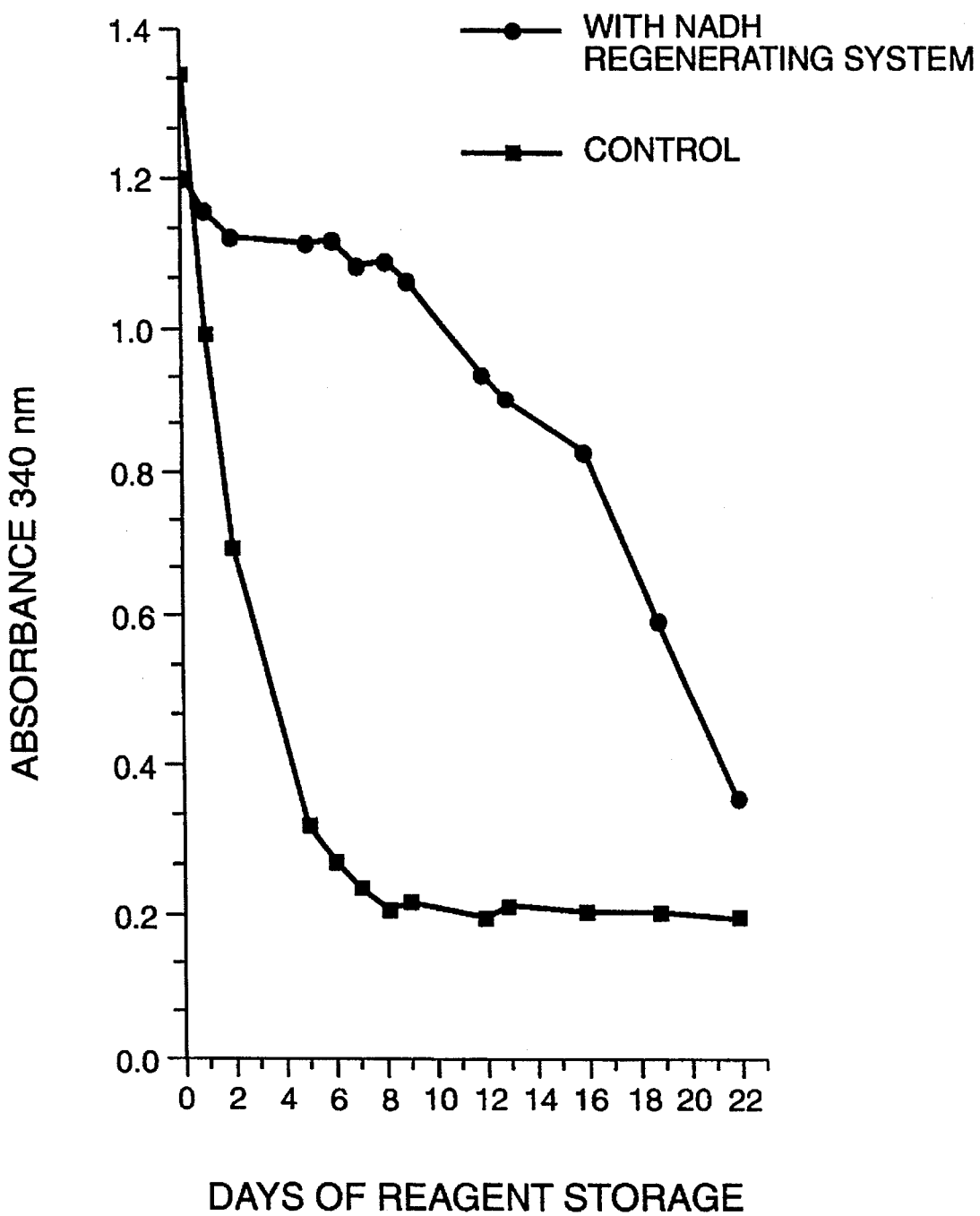
FIG. 5 shows the storage stability of the enzyme reagent for the two-reagent system after reconstitution.
Figure 6:
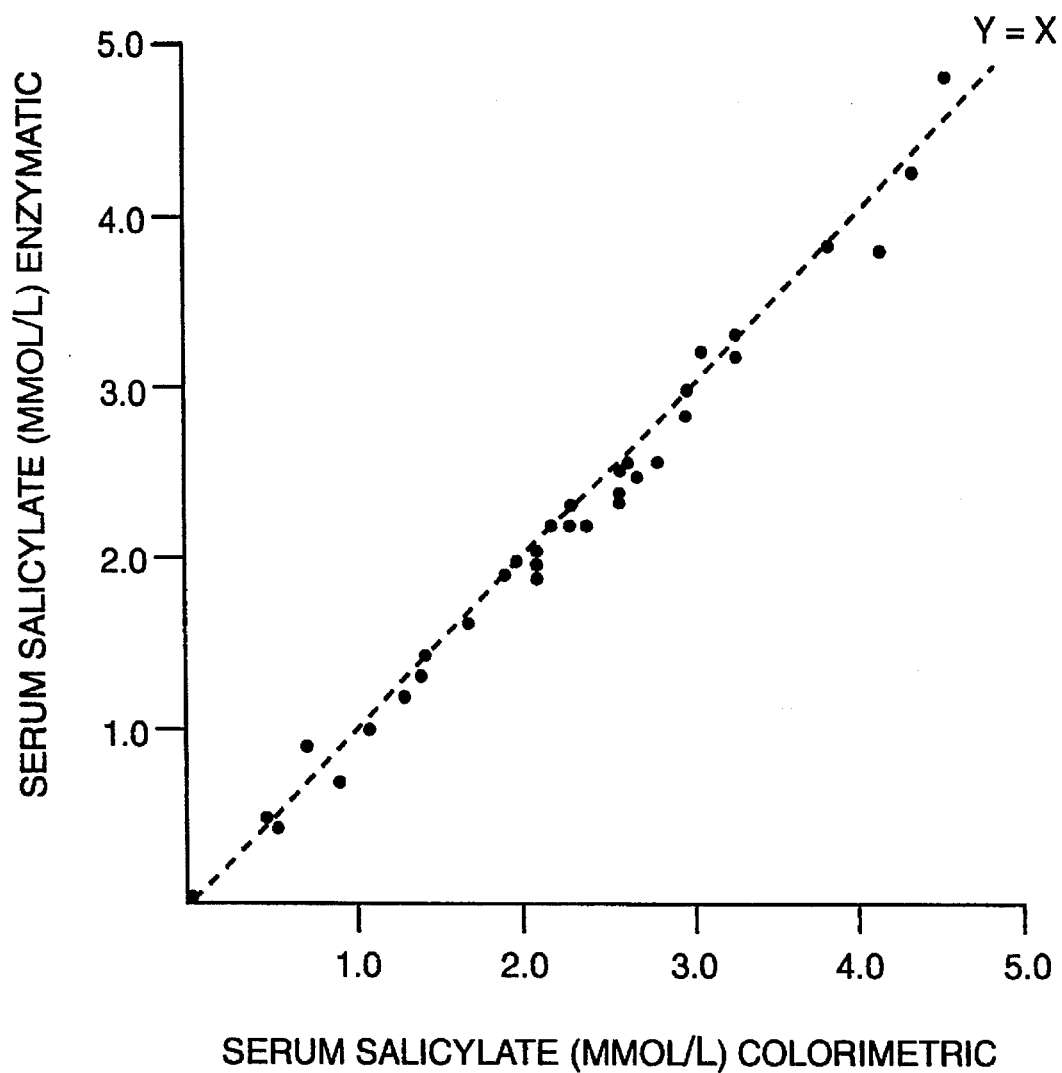
FIG. 6 shows a comparison of salicylate results using proposed enzymic procedure and routine colorimetric procedure.

Table 2.1(a) shows potential catechol reactants tested.

Table 2.1(b) shows those compounds tested in Table 2.1(a) which reacted with catechol.

Table 2.2(a) shows catechol reactions in various buffers.

Table 2.2(b) shows further catechol reactions in buffers.

Table 3(a) shows $\lambda$max for catechol reaction products.

Table 3(b) shows optimised catechol reaction systems.

Table 6a shows optimisation of 4-aminophenazone concentration in the manganese and carbonate buffer (pH10) system.

Table 7a shows the optimisation of sodium carbonate in the 4-aminophenazone reaction.

Table 8 shows the within day precision for proposed enzymic assay for salicylate and Table 9 shows the recovery of apparent salicylate level in the presence of potential interfering compounds where the potential interferents are present in the sample at a concentration of 10 mmol/L.

EXAMPLE 1

Effect of pH on Catechol Reactions

In this experiment, reactions were carried out at pH 8, 9, 10 and 14, to determine the effect of pH on any coloured product formation.

Method

Solutions of the potential reactants (50 mmol/L) were prepared, those insoluble in water being dissolved in ethanol. The compounds investigated are listed in Table 2.1a.

500 ul of aqueous catechol (50 mmol/L) were combined with 500 ul of reactant solution and incubated at room temperature for 10 minutes. Any observed colour change was noted.

2 mls of borate buffer (100 mmol/L) pH 8,9, 10 or sodium hydroxide solution (250 mmol/L) were then added and any colour changes noted after 10 and 60 minutes. A blank containing no catechol was set up for each reaction mixture.

Results

No compounds were found to react with catechol at pH 8.0. At pH 9, 10 and 14 several compounds were found to react, these are summarised in Table 2.1b.

EXAMPLE 1(a)

SALICYLATE Estimation (a single reagent system)

| Reagent | |
| --- | --- |
| Salicylate monooxygenase | 151 u/L |
| NADH or NADPH | 0.25 mmol/L |
| CHES buffer pH 10.0 | 145 mmol/L |
| Cobalt acetate | 0.25 mmol/L |
| 4-aminophenazone | 1.29 mmol/L |

Procedure

Serum sample (25 ul) was incubated with the reagent (1 ml) for 6 minutes. The absorbance at 520 nm was then determined. The results for serum samples containing various concentrations at salicylate are shown in Table 1.

TABLE 1

| Concentration of salicylate in serum (mmol/L) | A520nm |
| --- | --- |
| 1 | 0.151 |
| 2 | 0.300 |
| 3 | 0.435 |
| 4 | 0.592 |
| 5 | 0.746 |

EXAMPLE 2

Salicylate Estimation (two reagent system)

| Enzyme Reagent | |
| --- | --- |
| Salicylate monooxygenase | 304 u/L |
| NADH or NADPH | 1.52 mmol/L |
| Trig-HCl buffer pH 8.6 | 30 mmol/L |
| Manganese chloride | 0.15 mmol/L |
| 4-aminophenazone | 3.94 mmol/L |

Alkaline Reagent

Sodium carbonate solution
Whitconate AOS Li8

Procedure

Serum sample (25 ul) was incubated with enzyme reagent (330 ul) for 4 minutes. Alkaline reagent (1 ml) was then added and the absorbance at 520 nm was determined after 4 minutes. The results for serum samples containing various concentrations of salicylate are shown in Table 2.

TABLE 2

| Concentration of salicylate in serum (mmol/L) | A520 nm |
| --- | --- |
| 1 | 0.126 |
| 2 | 0.269 |
| 3 | 0.405 |
| 4 | 0.564 |
| 5 | 0.705 |

The following examples are given for the two reagent systems but they would be equally applicable to the one reagent system.

EXAMPLE 2(a)

Salicylate Estimation (two reagent system)

| Enzyme Reagent | |
| --- | --- |
| Sodium chloride | 100 mM |
| 4-aminophenazone | 4 mM |
| Manganese chloride | 0.15 mM |
| NADH | 4.5 mM |
| EPPS-pH 8.6 | 150 mM |
| Dextran (lyophilisation filler) | 2% |
| Bovine serum albumun | 2 mg/ml |
| Glucose | 4.5% |
| Glucose dehydrogenase | 0.1 u/ml |
| Salicylate monooxygenase | 2 units/ml |

| Alkaline reagent | |
| --- | --- |
| Sodium carobate | 150 mM |
| Witconate AOS | 0.05% |
| Sodium azide (preservative) | 0.1% |

Procedure

Serum sample (25 ul) was incubated with enzyme reagent (500 ul) for 4 minutes at room temperature. Alkaline reagent (1 ml) was then added and the absorbance at 520 nm was determined after incubation at room temperature for 4 minutes.

Procedure II (automated method)

The analyser parameters were set to pipette 5 ul of serum sample, 70 ul of enzyme reagent and 10 ul of water (wash) into one compartment of the analytical rotor; 140 ul of alkaline reagent and 10 ul of water (wash) was pipetted into the other compartment. After an incubation time of 4 minutes at 37° C. the rotor contents were mixed. After a further 2 mins the absorbance was read at 520 nm with a bichromatic blank reading taken at 600 nm five seconds later.

The results for serum samples containing various concentrations of salicylate are shown in Table 2a.

TABLE 2a

| Concentration of salicylate in serum (mmol/L) | A(520 nm – 600 nm) |
| --- | --- |
| 1 | 0.0656 |
| 2 | 0.1516 |
| 3 | 0.2355 |
| 4 | 0.3214 |
| 5 | 0.4084 |

EXAMPLE 3

Reduced Pyridine Nucleotide (NADH) Estimation

| Enzyme Reagent | |
| --- | --- |
| Salicylate monoxygenase | 304 u/L |
| Sodium salicylate | 5 mmol/L |
| Tris-HCl buffer pH 8.6 | 30 mmol/L |
| Manganese chloride | 0.15 mmol/L |
| 4-aminophenazone | 3.94 mmol/L |

EXAMPLE 4

Reduced Pyridine Nucleotide (NADPH) Estimation

Using identical reagents and procedures to those in example 3, a calibration curve for NADPH concentration was constructed. The results for this calibration are shown in Table 4.

TABLE 4

| Concentration of NADPH in serum (mmol/L) | A520 nm |
| --- | --- |
| 1 | 0.124 |
| 2 | 0.263 |
| 3 | 0.407 |
| 4 | 0.562 |
| 5 | 0.701 |

EXAMPLE 5

Lactate Estimation

Lactate concentration was estimated using the lactate dehydrogenase enzymatic reaction to reduce $NAD^+$ to NADH. The NADH generated was then estimated using the method of example 3.

| Enzyme Reagent | |
| --- | --- |
| Salicylate monooxygenase | 304 u/L |
| Sodium salicylate | 5 mmol/L |
| Tris-HCl buffer pH 8.6 | 30 mmol/L |
| Lactate dehydrogenase (E.C.1.1.1.27) | 100 u/L |
| Manganese chloride | 0.15 mmol/L |
| 4-aminophenazone | 3.94 mmol/L |

| Alkaline Reagent | |
| --- | --- |
| Sodium carbonate solution | 120 mmol/L |
| Whitconate AoS Li8 | 0.05% |

Procedure

330 μl enzyme reagent was incubated with 25 μl serum sample containing lactate for 4 minutes. One ml alkaline reagent was added and the absorbance at 520 nm was determined after 4 minutes. The results for various serum lactate concentrations are given in Table 5.

TABLE 5

| Concentration of lactate in serum (mmol/L) | A520 nm |
| --- | --- |
| 1 | 0.124 |
| 2 | 0.264 |
| 3 | 0.406 |
| 4 | 0.562 |
| 5 | 0.711 |

EXAMPLE 6

Glucose estimation

Glucose concentration was estimated using ATP and hexokinase enzyme to convert all the glucose to glucose-6-phosphate. The enzyme glucose-6-phosphate dehydrogenase was then used to convert $NAD^+$ to NADH, which was detected by the method as described in example 3.

| Enzyme reagent | |
| --- | --- |
| Salicylate monooxygenase | 304 u/L |
| Sodium salicylate | 5 mmol/L |
| Tris-HCl buffer pH8.6 | 30 mmol/L |
| Magnesium chloride | 2 mmol/L |
| $NAD^+$ | 5 mmol/L |
| Glucose-6-phosphate dehydrogenase (E.C.1.1.1.49) | 100 u/L |
| Manganese chloride | 0.15 mmol/L |
| 4-aminophenazone | 3.94 mmol/L |

| Alkaline reagent | |
| --- | --- |
| sodium carbonate solution | 120 mmol/L |
| whitconate AoS Li8 | 0.05% |

Procedure

Serum sample (25 μl) was first reacted with an excess of ATP and hexokinase enzyme (E.C.2.7.1.1). 330 μl. enzyme reagent was added and the mixture was incubated for 4 minutes. Alkaline reagent (1 ml) was added and the absorbance at 520 nm was determined after 4 minutes.

The results for various concentrations of glucose are given in Table 6.

TABLE 6

| Concentration of glucose in serum (mmol/L) | A520 nm |
| --- | --- |
| 1 | 0.122 |
| 2 | 0.264 |
| 3 | 0.413 |
| 4 | 0.570 |
| 5 | 0.713 |

EXAMPLE 7

Acetyl Salicylate Estimation

Acetyl salicylate in the sample was first hydrolysed to salicylate and and acetate by the aryl ester hydrolase enzyme. The liberated salicylate was then assayed by the method given in example 2.

| Enzyme Reagent | |
| --- | --- |
| Aryl ester hydolase (E.C.3.1.1.2) | 200 u/L |
| Salicylate monooxygenase | 304 u/L |
| NADH or NADPH | 1.52 mmol/L |
| Tris-HCl buffer pH 8.6 | 30 mmol/L |
| Manganese chloride | 0.15 mmol/L |
| 4-aminophenazone | 3.94 mmol/L |

| Alkaline Reagent | |
| --- | --- |
| Sodium carbonate solution | 120 mmol/L |

-continued

| Alkaline Reagent | |
|---|---|
| Whitconate AoS Li8 | 0.05% |

Procedure

25 μl serum sample containing acetyl salicylate was incubated with 330 μl enzyme reagent for 4 minutes. One ml alkaline reagent was added and the absorbance at 520 nm was determined after 4 minutes. The results for various acetyl salicylate concentrations are given in Table 7.

TABLE 7

| Concentration of acetyl salicylate in serum (mmol/L) | A520 nm |
|---|---|
| 1 | 0.130 |
| 2 | 0.274 |
| 3 | 0.412 |
| 4 | 0.570 |
| 5 | 0.715 |

TABLE 2.1a

| Potential Catechol Reactants | |
|---|---|
| Water Soluble Compounds | Alcohol Soluble Compounds |
| Antipyrine | p-Aminohippuric acid |
| Amidol | 2-Aminopyrazine |
| Aniline oxalate | 1-Aminoanthraquinone |
| o-Aminobenzoic acid | 2-Aminobenzothiazole |
| 4-Aminophenazone | 6-Aminobenzothiazole |
| 5-Aminoquinone | 6-Amino-2-phenylindenone |
| 4-Aminoacetophenone | 2-Amino-4-methylbenzothiazole |
| 2-Aminobiphenyl | 2,6-Dichloro-p-benzoquinone-4-chlorimine |
| 3-Amino-5-6,dimethyltriazine | 2,6-Dichloro-quinone-4-chloro-imide |
| 2-Aminobenzimidazole | 4-Hexylresorcinol |
| 4-Nitrophenol | 8-Hydroxyquinoline |
| Napthoresorcinol | 4-Dimethylaminobenzaldehyde |
| Phloroglucinol | 4-Nitroaniline |
| m-Phenylenediamine | o-Phenylenediamine |
| Resorcinol | |
| β-Resorcylic acid | |
| 4,2-Thiazolylazoresorcinol | |

TABLE 2.1b

| | | Compounds which Reacted with Catechol | | | |
|---|---|---|---|---|---|
| | | Colour of Reactant | Colour of Reactant & | Colour on Addition of Alkali | | Blank |
| Reactant | pH | Solution | Catechol | 10 mins | 60 mins | 60 mins |
| p-Amino-hippuric acid | 9 | | | Colourless | Pink | Colourless |
| | 10 | Colourless | Colourless | Pink | Red | Colourless |
| | 14 | | | Red | Brown | Colourless |
| 4-Dimethylaminobenzaldehyde | 10 | Coloureless | Colourless | Colourless | Pink | Colourless |
| | 14 | | | Colourless | Pink | Colourless |
| 4-Aminophenazone | 10 | Pale yellow | Colourless | Pale Pink | Pink | Colourless |
| | 14 | | | Red | Brown | Colourless |
| Antipyrine | 10 | Colourless | Colourless | Colourless | Brown | Colourless |
| | 14 | | | Colourless | Brown | Colourless |
| 2-Aminobenzothiazole | 10 | Colourless | Colourless | Colourless | Purple | Colourleas |
| | 14 | | | Colourless | Green | Colourless |
| 6-Aminobenzothiazole | 10 | Colourless | Colourless | Pink | Purple | Colourless |
| | 14 | | | Green | Brown | Colourless |
| 2-Amino-4-methylbenzothiazole | 10 | Colourless | Colourless | Pink | Purple | Colourless |
| | 14 | | | Pink | Brown | Colourless |
| 4-Aminoacetophenone | 10 | Colourless | Colourless | Pink | Purple | Colourless |
| | 14 | | | Pink | Brown | Colourless |
| O-Aminobenzoic Acid | 14 | Colourless | Colourless | Orange | Brown | Colourless |
| Aniline oxalate | 14 | Colourless | Colourless | Orange | Brown | Colourless |
| Resorcinol | 14 | Colourless | Colourless | Orange | Brown | Colourless |
| β-Resorcyclic acid | 14 | Colourless | Colourless | Red | Brown | Colourless |
| 3-Amino-5,6-dimethyl-triazine | 14 | Colourless | Colourless | Green | Brown | Colourless |

TABLE 2.2a

Catechol Reactions in Various Buffers

| Legend | Reactant | Colour of Reactant Solution | Glycine pH 9.5 Colour 10 mins | 1 hour | Carbonate pH 9.5 Colour 10 Mins | 1 hour | AMP pH 9.5 Colour 10 mins | 1 hour | AMPD pH 9.5 Colour 10 mins | 1 hour |
|---|---|---|---|---|---|---|---|---|---|---|
| 1 | p-Amino-hippuric acid | Colourless | Colourless | Pale pink | Orange | Red | Orange | Orange | Orange | Red |
| 2 | Dimethyl-amino-benzaldehyde | Colourless | Pale pink | Pale pink | Pale Orange | Brown | Pale pink | Pink | Colourless | Brown |
| 3 | 4-Amino-phenazone | Pale yellow | Pink | Brown | Red | Red | Red | Red | Red | Red |
| 4 | Antipyrine | Colourless | Pale pink | Pale pink | Colourless | Pink | Colourless | Pale Brown | Pink | Brown |
| 5 | 2-Aminobenzo-thiazole | Colourless | Pale pink | Pale pink | Pale pink | Brown | Pink | Brown | Pink | Brown |
| 6 | 6-Aminobenzo-thiazole | Colourless | Pink | Orange | Red | Red | Orange | Orange | Orange | Orange |
| 7 | 2-Amino-4-methyl-benzothiazole | Colourless | Pale pink | Pale pink | Pink | Brown | Pale pink | Pink | Pink | Brown |
| 8 | 4-Aminoace-tophenone | Colourless | Pale pink | Pale pink | Pale pink | Pale pink | Orange | Orange | Orange | Orange |
| 9 | o-Aminobenzoic acid | Colourless | Colourless | Pale pink | Pink | Red | Orange | Red | Orange | Red |
| 10 | Aniline Oxalate | Colourless | Colourless | Pale pink | Colourless | Pale pink | Colourless | Orange | Colourless | Orange |
| 11 | Resorcinol | Colourless | Green | Yellow | Green | Orange | Green | Orange | Green | Orange |
| 12 | β-Resorcylic acid | Colourless | Colourless | Colourless | Pale Green | Green | Green | Brown | Green | Brown |
| 13 | 3-Amino-5,6-dimethyl-triazine | Colourless | Pale pink | Pale pink | Pink | Brown | Pale pink | Pale pink | Pale pink | Brown |

TABLE 2.2b

Catechol Reactions in Various Buffers

| Legend | Reactant | Colour of Reactant Solution | Ciethanolanine pH 9.0 Colour 10 mins | 1 hour | TAPS pH 9.3 Colour 10 mins | 1 hour | Glycylglycine 9.5 Colour 10 mins | 1 hour | Borate pH 10 Colour 10 mins | 1 hour |
|---|---|---|---|---|---|---|---|---|---|---|
| 14 | p-Amino-hippuric acid | Colourless | Colourless | Colourless | Pink | Pink | Colourless | Colourless | Pale pink | Pink |
| 15 | Dimethylamino-benzaldehyde | Colourless | Colourless | Colourless | Colourless | Pale pink | Colourless | Colourless | Colourless | Pink |
| 16 | 4-Aminophena-zone | Pale yellow | Pink | Pink | Pink | Red | Pink | Pale Brown | Pink | Red |
| 17 | Antipyrine | Colourless | Pink | Yellow | Pale pink | Orange | Colourless | Colourless | Colourless | Brown |
| 18 | 2-Aminobenzo-thiazole | Colourless | Pink | Yellow | Colourless | Pale pink | Colourless | Colourless | Pink | Pink |
| 19 | 6-Aminobenzo-thiazole | Colourless | Colourless | Pink | Pink | Red | Pale Pink | Pink | Pink | Orange |
| 20 | 2-Amino-4-methyl-benzothiazole | Colourless | Pink | Yellow | Colourless | Pale orange | Colourless | Colourless | Pink | Orange |
| 21 | 4-Aminoace-tophenone | Colourless | Colourless | Colourless | Pink | Pink | Colourless | Pale pink | Colourless | Pink |
| 22 | o-Aminobenzoic acid | Colourless | Pink | Yellow | Pink | Pink | Colourless | Pink | Orange | Brown |
| 23 | Aniline oxalate | Colourless | Colourless | Colourless | Colourless | Pale pink | Colourless | Colourless | Colourless | Colourless |
| 24 | Resorcinol | Colourless | Pale Green | Green | Green | Orange | Green | Green | Colourless | Green |
| 25 | β-Resorcyclic acid | Colourless | Colourless | Yellow | Colourless | Pale pink | Colourless | Colourless | Pink | Brown |
| 26 | 3-Amino5,6-dimethyl-triazine. | Colourless | Brown | Yellow | Colourless | Orange | Colourless | Colourless | Pink | Brown |

TABLE 3a $\lambda_{max}$ for Catechol Reaction Products

| System Details | | | Absorbance | Absorbance | ΔAbsorbance |
|---|---|---|---|---|---|
| Reactant | Buffer | $\lambda_{max}$ | at $\lambda_{max}$ | Blank | at $\lambda_{max}$ |
| p-Amino-hippuric acid | Carbonate pH 9.5 | 475 nm (peak) | 1.200 | 0.025 | 1.175 |
| 4-Aminophenazone | Carbonate pH 9.5 | 520 nm (shoulder) | 0.830 | 0.010 | 0.820 |
| 2-Aminobenzothiazole | Diethanolamine pH 9.5 | 430 nm (peak) | 0.460 | 0.030 | 0.430 |
| 6-Aminobenzothiazole | AMP pH 9.5 | 475 nm (peak) | 1.180 | 0.010 | 1.170 |
| 4-Aminoacetophenone | Carbonate pH 9.5 | 470 nm (peak) | 0.870 | 0.010 | 0.860 |
| o-Aminobenzoic acid | AMPD pH 9.5 | 520 nm (peak) | 0.370 | 0.024 | 0.346 |
| Resorcinol | AMP pH 9.5 | 420 nm (shoulder) | 0.370 | 0.030 | 0.330 |
| Resorcinol | AMP pH 9.5 | 475 nm (peak) | 0.580 | 0.020 | 0.560 |
| 2-Amino-4-methyl-benzothiazole | Carbonate pH 9.5 | 475 nm (peak) | 0.430 | 0.020 | 0.410 |

TABLE 3.b

Optimised Catechol Reaction Systems (Concentrations in Final Reaction Mixture)

| Concentration Reactant (mmol/L) | Concentration Metal Ions (mmol/L) | Concentration Buffer (mmol/L) | $\lambda_{max}$ of Reaction Product |
|---|---|---|---|
| 4-Aminophenazone (0.64) | Cobalt (0.25) | Carbonate pH 10 (75) | 520 nm |
| | Manganese (0.025) | Carbonate pH 10 (75) | 520 nm |
| | Manganese (0.025) | AMPD pH 9.5 (75) | 520 nm |
| | Manganese (0.025) | AMP pH 10 (75) | 520 nm |
| Resorcinol (0.256) | Magnesium (0.25) | Sodium hydroxide (19) | 550 nm |
| | Manganese (0.25) | Sodium hydroxide (19) | 550 nm |
| 6-Aminobenzothiazole (1.28) | Manganese (0.05) | Carbonate pH 10 (75) | 475 nm |
| | Cobalt (0.25) | Carbonate pH 10 (75) | 475 nm |
| o-Aminobenzoic acid (1.28) | Manganese (0.05) | Carbonate pH 10 (75) | 475 nm |
| p-Amino-hippuric acid (1.28) | Cobalt (0.25) | Carbonate pH 10 (75) | 475 nm |

TABLE 6(a)

Optimisation of 4-Aminophenazone Concentration in the Manganese + Carbonate Buffer (pH 10) System

| Concentration 4-Aminophenazone (mmol/L) | A 520 nm Plateau | Blank |
|---|---|---|
| 50 | 1.151 (3 mins) | 0.011 |
| 30 | 1.159 (3 mins) | 0.010 |
| 10 | 1.171 (3 mins) | 0.006 |
| 5 | 1.170 (3 mins) | 0.006 |

TABLE 7(a)

Optimisation of Sodium Carbonate Concentration in the 4-Aminophenazone Reaction

| Conc. of Sodium Carbonate Solution (mmol/L) | A520 nm (plateau) | Time to Plateau (minutes) |
|---|---|---|
| 600 | 0.768 | 2.0 |
| 400 | 0.774 | 2.5 |
| 200 | 0.753 | 2.5 |
| 100 | 0.750 | 3.5 |
| 50 | 0.746 | 5.0 |

TABLE 8

Within day precision for proposed enzymatic assay for salicylate.

| Mean (mmol/L) | S.D. | C.V. (%) | n |
|---|---|---|---|
| 1.03 | 0.0488 | 4.6 | 15 |
| 4.14 | 0.0516 | 1.2 | 15 |

TABLE 8-continued

Within day precision for proposed enzymatic assay for salicylate.

| Mean (mmol/L) | S.D. | C.V. (%) | n |
|---|---|---|---|

CV—Coefficient of variation
SD—Standard deviation
n—no. of samples in test

TABLE 9

Recovery of apparent salicylate level in the presence of potential interfering compounds. All potential interferents were present in the sample at a concentration of 10 mmol/L.

| Compound Present | Salicylate Conc Observed (mmol/L) | Salicylate Recovery (%) |
|---|---|---|
| None, ie serum control | 2.05 | 100 |
| Salicyluric acid | 2.15 | 105 |
| Gentisic acid | 2.30 | 112 |
| Benzoate | 2.05 | 100 |
| 4 Hydroxybenzoate | 2.00 | 98 |
| L-Tyrosine | 2.05 | 100 |
| 4 Aminosalicylate | 2.05 | 100 |
| Acetoacetate | 2.10 | 102 |
| 3-Hydroxybutyrate | 2.08 | 101 |

We claim:

1. A method for the estimation of a salicylate in a sample consisting essentially of the steps of:

(a) enzymatically converting the salicylate to a catechol by the action of a salicylate mono-oxygenase enzyme on the salicylate in the presence of a reduced pyridine nucleotide selected from the group consisting of nicotinamide adenine dinucleotide phosphate (NADPH) and nicotinamide adenine dinucleotide (NADH) at a pH of 6.0 to 10.5, and then (b) reacting the catechol produced with 4-aminophenazone wherein reaction (b) is carried out at an alkaline pH and forms an ultra-violet, visible or infra-red electromagnetic radiation absorbing dye, the quantity of which can be estimated colorimetrically.

2. The method as claimed in claim 1 wherein steps (a) and (b) are carried out at pH10.

3. The method as claimed in claim 1 wherein step (a) is carried out at pH8.6 and step (b) is carried out at pH10.

4. The method as claimed in claim 1 wherein the concentration of the 4-aminophenazone is 0.5–50 mmol/L.

5. The method as claimed in claim 1 wherein conversion of salicylate to catechol and the conversion of catechol to dye is performed in a one step reaction where all the reagents are present together.

6. The method as claimed in claim 1 wherein the conversion of salicylate to catechol and the conversion of catechol to dye is performed in two successive steps.

7. The method as claimed in claim 1 wherein lithium lactate and lactate dehydrogenase are used to reduce the pyridine nucleotide.

8. The method as claimed in claim 1 wherein metal ions are added to catalyse the enzymatic conversion.

9. The method as claimed in claim 8 wherein the metal ions are manganese or cobalt.

10. The method as claimed in claim 1 wherein the pH is controlled by a buffer selected from the group consisting of carbonate-bicarbonate, borate, glycine, diethanolamine, glycylglycine, sodium phosphate, potassium phosphate, Tris HCl, 2-N-cyclohexylamine ethanesulphonic acid (CHES), 2-amino 2-methyl-1 propanol (AMP), 2-amino 2-methyl-1, 3-propandiol (AMPD), N-Tris (hydroxymethyl) methyl-3-amino propanesulphonic acid (TAPS), 3 cyclohexyl (amino)-1-propane sulphonic acid (CAPS), N-2-hydroxy-ethyl-piperazine-N-2-ethanesulphonic acid (HEPES) and N-2-hydroxyethyl-piperazine-N-3-propanesulphonic acid (EPPS).

11. The method according to claim 1 wherein the production of dye is effected in the presence of the buffer 2-N-cyclohexylamine ethanesulphonic acid (CHSS) at pH 10.

12. The method according to claim 1 wherein the production of dye is effected by mixing sodium carbonate buffer with an enzyme reagent containing N-2-hydroxyethyl-piperazine-N-3-propanesulphonic acid at a pH of 8.6 and which has been used to convert salicylate to catechol.

13. The method according to claim 1 wherein reagents are provided in a lyophilized form.

14. A diagnostic kit for estimating a salicylate in a sample including the steps of (a) enzymatically converting the salicylate to a catechol by the action of a salicylate mono-oxygenase enzyme on the salicylate in the presence of a reduced pyridine nucleotide selected from the group consisting of nicotinamide adenine dinucleotide phosphate (NADPH) and nicotinamide adenine dinucleotide (NADH) at a pH of 6.0 to 10.5, and then (b) reacting the catechol produced with 4-aminophenazone wherein reaction (b) is carried out at an alkaline pH and forms an ultra-violet, visible or infra-red electromagnetic radiation absorbing dye, wherein the kit contains:

(1) a container containing the salicylate mono-oxygenase enzyme suitable to convert the salicylate in the sample to a catechol in the presence of the reduced pyridine nucleotide, the enzyme in solution having a pH of 6.0 to 10.5, and (2) a container containing a compound suitable for the conversion of the catechol to a dye.

15. The diagnostic kit as claimed in claim 14 wherein the pyridine nucleotide is immobilized on a solid or semi-solid support.

16. The diagnostic kit as claimed in claim 14 wherein the enzyme and the pyridine nucleotide are provided in the same solution.

17. The diagnostic kit as claimed in claim 14 wherein the enzyme is provided in an aqueous solution having a pH of 6.0 to 10.5.

* * * * *